(12) United States Patent
Graf et al.

(10) Patent No.: US 7,316,670 B2
(45) Date of Patent: Jan. 8, 2008

(54) ADMINISTERING APPARATUS COMPRISING A DOSAGE DISPLAY

(75) Inventors: Roney Graf, Burgdorf (CH); Fritz Kirchhofer, Sumiswald (CH)

(73) Assignee: TecPharma Licensing AG, Burgdorf (CH)

( * ) Notice: Subject to any disclaimer, the term of this patent is extended or adjusted under 35 U.S.C. 154(b) by 0 days.

(21) Appl. No.: 10/621,970

(22) Filed: Jul. 17, 2003

(65) Prior Publication Data

US 2004/0019333 A1    Jan. 29, 2004

(30) Foreign Application Priority Data

Jul. 17, 2002    (DE) ............................... 102 32 410

(51) Int. Cl.
*A61M 5/00* (2006.01)

(52) U.S. Cl. ................. 604/207; 604/211; 604/208

(58) Field of Classification Search ............... 604/131, 604/134, 135, 187, 207–211, 218, 224; 60/131, 60/134, 135, 187, 207–211, 217, 224
See application file for complete search history.

(56) References Cited

U.S. PATENT DOCUMENTS

| | | | | |
|---|---|---|---|---|
| 4,865,591 A | * | 9/1989 | Sams | 604/186 |
| 4,936,833 A | * | 6/1990 | Sams | 604/232 |
| 5,295,976 A | * | 3/1994 | Harris | 604/211 |
| 5,728,074 A | * | 3/1998 | Castellano et al. | 604/207 |
| 6,086,567 A | * | 7/2000 | Kirchhofer et al. | 604/211 |
| 6,228,067 B1 | | 5/2001 | Gabriel | |
| 6,277,101 B1 | | 8/2001 | Kirchhofer et al. | |
| 2003/0004467 A1 | * | 1/2003 | Musick et al. | 604/218 |

FOREIGN PATENT DOCUMENTS

| | | |
|---|---|---|
| WO | WO 95/04563 | 2/1995 |
| WO | WO 97/36625 | 10/1997 |

\* cited by examiner

*Primary Examiner*—Kevin C. Sirmons
*Assistant Examiner*—Elizabeth MacNeill
(74) *Attorney, Agent, or Firm*—David E. Bruhn (57) ABSTRACT

An administering apparatus with a dosage display, including a casing, a reservoir for a fluid product, a driven device which acts on the product, a dosing means for selecting a product dosage to be delivered which includes a dosage scale including a number of dosage marks axially spaced from each other, and a drive device coupled to the driven device for driving the driven device, the drive device performing a delivery stroke from an initial position, in a drive direction, to a delivery stopper, the length of the delivery stroke counter to the drive direction being limited by selecting the product dosage using the dosing means, wherein the casing is transparent at least in an area overlapping the dosage scale, and wherein the drive device forms an indicator to the dosage scale in order to indicate the initial position of the drive device.

27 Claims, 5 Drawing Sheets

ADMINISTERING APPARATUS COMPRISING A DOSAGE DISPLAY

CROSS-REFERENCE TO RELATED APPLICATION

This application claims priority of German Patent Application No. 102 32 410.7, filed on Jul. 17, 2002.

BACKGROUND

The invention relates to administering devices and methods. More particularly, it relates to an administering apparatus or device with a dosage display which allows a product dosage to be selected, and to a method of providing a dosage display. The administering device of the present invention may be used in medical, veterinary, therapeutic, diagnostic, pharmaceutical and/or cosmetic applications. One preferred example of administering apparatus in accordance with the present invention is injection apparatus, including injection pens. Other examples of administering apparatus according to the invention can include inhalation apparatus or apparatus for administering liquid nutrients in doses.

Administering apparatus which allow a dosage to be selected naturally have a dosage display in order to indicate the selected product dosage to be administered to the user of the apparatus. A reliable dosage display is essential for selecting and administering the desired product dosage.

In the injection apparatus known from U.S. Pat. No. 6,228,067, an optical dosage display is provided between two casing sleeves which can be rotated relative to each other, for selecting a dosage. The two casing sleeves overlap each other. A dosage scale is printed onto the inner casing sleeve in the overlapping area, the scale consisting of a sequence of dosage numbers representing dosage units. The outer casing sleeve in the overlapping area is transparent in the area of the dosage scale, by comprising an opening there which serves as a viewing window. To select a dosage, the two casing sleeves are rotated relative to each other. The injection apparatus further comprises a dosing sleeve arranged in the overlapping area between the two casing sleeves which is axially moved relative to the casing sleeves, to select the dosage. The dosing sleeve likewise comprises a viewing window for reading the dosage scale. The dosage scale is read through the two superimposed viewing windows of the dosing sleeve and the outer casing sleeve.

The selected product dosage can indeed be reliably read with the aid of this dosage scale. However, the user then only knows that he has selected the desired dosage. It remains uncertain whether the entire dosage or only a part of it, for example because evacuation of a product reservoir is already in progress, can be administered in the next injection.

SUMMARY

It is one object of the invention to provide a dosage display which gives reliable information about a product dosage which can actually be administered.

In one embodiment, the present invention comprises an administering apparatus with a dosage display, including a casing, a reservoir for a fluid product, a driven device which acts on the product, a dosing means for selecting a product dosage to be delivered comprising a dosage scale comprising a number of dosage marks axially spaced from each other, and a drive device coupled to the driven device for driving the driven device, wherein the casing is transparent at least in an area overlapping the dosage scale, and wherein the drive device forms an indicator relative to the dosage scale to indicate the initial position of the drive device.

The invention relates to a dosage display of an administering apparatus. In one embodiments, the administering apparatus comprises a casing which accommodates a reservoir for a fluid product or forms said reservoir itself. A product container which is accommodated in the casing, for example, an ampoule, can form the reservoir. A conveying device of the administering apparatus, mounted by the casing, comprises a driven device and a drive device which are coupled to each other in order to deliver product out of the reservoir, i.e., to convey product out of the reservoir through an outlet of the reservoir, to be administered. The driven device acts on the product, and is driven for this purpose by the drive device.

The administering apparatus further comprises a dosing means, using which a product dosage to be delivered can be selected. The drive device can be moved from an initial position in a drive direction up to a delivery stopper which is formed by the casing or can at least be fixed such that it cannot move relative to the casing with respect to the drive direction. The length, measured in the drive direction, of this delivery stroke of the drive device is set by selecting the product dosage by means of the dosing means. The delivery stroke is preferably a linear translational movement, but can in principle also be performed along a curved arc and can also be or comprise a rotational movement.

The dosing means comprises a dosage scale having a number of dosage marks for optically displaying dosage units. Preferably, in one embodiment, each product dosage, measured in dosage units, which can be selected is precisely allocated one dosage mark from the number of dosage marks. The dosage marks are spaced out from each other in the drive direction, such that each dosage mark from the number of dosage marks assumes a different height with respect to the drive direction, preferably an axial line corresponding to the drive direction.

The casing is transparent, at least in an area which overlaps the dosage scale. When it is mentioned in this context that the transparent area overlaps the dosage scale, then "overlap" is intended merely to mean that the dosage scale can be read in the transparent area of the casing. This can be achieved by providing the casing with an opening through which the dosage scale can be entirely or only partially read. More preferably, however, in one embodiment, the casing itself is a support for the dosage scale in the transparent area, for example by printing the dosage scale on an inner or outer surface of said area of the casing consisting of transparent material or forming it in the transparent casing material. Thus, the dosing scale can be produced in a transparent casing material of suitable material composition by means of laser irradiation. It is sufficient for the purposes of the invention if the casing is only transparent in the area overlapping the dosage scale. The casing may, however, also be completely transparent.

According to the invention, the drive device forms an indicator of the dosage scale whose axial position relative to the dosage scale can be read due to the transparency of the casing, in order to display the sited initial position of the drive device through the casing, relative to the dosage marks spaced out in the drive direction. The dosage scale is therefore a length scale extending in the drive direction, whose length units are the dosage marks spaced out in the drive direction. By reading, i.e., comparing, the position of the indicator of the drive device on this length scale, the user knows what delivery stroke the drive device will perform when the drive device is moved from its initial position in the drive direction up to the delivery stopper. Precisely when the drive device assumes a front end position in which it abuts the delivery stopper, the indicator of the drive device assumes the zero position on the dosage scale corresponding to a zero dosage.

In one preferred embodiment, the dosage marks spaced out in the drive direction are bar marks, each of said dosage marks formed by precisely one bar mark which extends over a particular length perpendicular to the drive direction and is advantageously as fine as possible. The indicator formed by the drive device is preferably also a bar or comprises a bar which points parallel to the bar marks. In principle, the indicator of the drive device can also be arrow-shaped or can exhibit a different shape suitable for an indicator, said shape enabling the position of the drive device on the dosage scale as compared to the dosage marks to be reliably identified.

In one preferred embodiment, the dosage scale additionally comprises dosage symbols which each represent a particular dosage, each of the symbols representing a different dosage. These dosage symbols, which are preferably dosage numbers corresponding directly to the dosage units, can also simultaneously form the spaced out dosage marks, by being appropriately shaped. Preferably, however, the dosage marks in accordance with the invention are provided in addition to such dosage symbols. In one embodiment, each of the dosage marks is allocated a dosage symbol in its immediate vicinity, such that the user can not only read the exact position of the display device, measured in the drive direction, on the dosage scale, but simultaneously also the dosage corresponding to this position, symbolically or directly in the form of a dosage number.

In one embodiment, the dosing means also comprises a dosage scale for optically displaying the product dosage selected. In one embodiment, the dosage scale on which the position of the drive device can be read also simultaneously forms the dosage scale for displaying the product dosage selected. In principle, however, it would also be conceivable to provide a separate dosage scale for each of these two dosage displays. In combination, the two integrated or independent dosage displays provide a display of the remaining amount. If, namely, a product dosage is selected which exceeds a remaining dosage still available in the reservoir, then comparing the dosage displays provides the user with a reliable indication that the selected product dosage can no longer actually be delivered or has not actually been delivered. Which of these two pieces of information the user receives depends on the type of coupling between the driven device and the drive device. In one case, the drive device cannot be moved up to the delivery stopper, such that the dosage display in accordance with the invention displays this state after administering. In one preferred embodiment, the drive device can only be moved relative to the driven device, opposite or counter to the drive direction, by a path length which corresponds to the remaining dosage still left in the reservoir. In this case, the user can directly read the remaining dosage left before delivery and, by comparing it with the display of the product dosage selected, determine the missing dosage. In this preferred variant of the coupling between the driven device and the drive device, the driven device forms a reverse stopper, which is the maximum to which the drive device can be moved counter to the drive direction, relative to the driven device.

For selecting the product dosage, the dosing means comprises a dosing member which forms the dosing stopper for the drive device. In one embodiment, the drive device can be moved counter to the drive direction up to said dosing stopper. A slight distance between the delivery stopper and the dosing stopper, as viewed in the drive direction, corresponds to the delivery stroke of the drive device, wherein however a deduction is to be made for the formation of a front and a rear stopper area of the drive device, measured in the drive direction.

The dosage scale for displaying the product dosage selected can be connected to the dosing member. In one preferred embodiment, however, it is connected to the casing, in particular when the same dosage scale also forms the display for the position of the drive device. If the dosage scale is connected to the casing, the dosing member forms an indicator whose position relative to said dosage scale indicates the product dosage selected. The indicator of the dosing member is formed by a viewing window, which may, in one embodiment, be developed into a magnifier.

Operational comfort is accommodated if the product dosage selected and the position of the drive device measured in the drive direction can be read in one glance, i.e., simultaneously. Expediently, the position of the drive device and the product dosage selected can be read alongside each other in the drive direction, providing the position of the drive device does not already exactly correspond to the product dosage selected. In one embodiment, if the product dosage selected is delivered from the initial position of the drive device by the delivery stroke, the indicator of the drive device and the indicator for displaying the product dosage selected overlap.

In one preferred embodiment, the dosing member can be moved translationally in the drive direction and/or counter to the drive direction, to adjust the dosing stopper. Its dosing movement is a combination of the translational movement and a rotational movement about the translational axis. In principle, however, the dosing movement of the dosing member could also be a purely translational or purely rotational movement. For one preferred embodiment of the combined rotational and translational movement, the dosing member is coupled to the casing via a swivel joint, preferably a screw joint, such that the rotational movement of the dosing member causes its translational movement.

If the dosing movement of the dosing member is a combined rotational and translational movement, wherein the rotational axis corresponds to the translational axis, then the dosage scale for displaying the product dosage selected is advantageously a sequence of dosage symbols, e.g., dosage numbers, running spirally around the rotational axis. As already explained, the same dosage scale can also form the dosage scale for displaying the position of the drive device, by allocating its dosage marks to the dosage symbols or by realizing them using the dosage symbols themselves, by appropriately representing them. In one embodiment, it is particularly advantageous if the indicator of the drive device extends circumferentially around the rotational axis of the dosing member, for example as a fine, intermittent or preferably continuous line, such that the indicator of the drive device can be read on the dosage scale in any rotational angular position of the dosing member.

In one preferred embodiment, the dosing member comprises an inner dosing body and an outer dosing body, between which a slight gap remains in an overlapping area. The inner dosing body protrudes into the casing. The casing protrudes into the slight gap. The outer dosing body can in particular form a gripping part of the dosing member. The dosing bodies are preferably arranged such that the dosing member can be rotated relative to the casing engaging with the gap. The nested arrangement of an inner dosing body and an outer dosing body allows the dosing member to be designed axially short. By producing the two dosing bodies separately, the dosing member can be more simply equipped than in the case of producing them as one piece having a higher functionality. If produced separately, the inner dosing body and the outer dosing body may be suitably connected to each other such that a translational movement between the dosing bodies along a translational axis and a rotational movement about the translational axis are not possible, but rather one dosing body slaves the other.

In one embodiment, the driven device preferably comprises a piston which is accommodated in the reservoir such that it can axially move in an advancing direction towards an outlet of the reservoir, in order to deliver product from the reservoir. In this embodiment, the driven device also comprises a piston rod. The driven device directly engages with the piston rod. The piston rod can be formed together with the piston as one piece or can be fixedly connected to the piston, for example by means of a screw connection or a fixed plug connection. In one preferred embodiment, however, the piston rod is formed as a separate part from the piston, said part pressing against the piston to deliver the product in the advancing direction. If the product is conveyed by means of a piston, then the advancing direction of the piston and the drive direction correspond.

In one embodiment, the driven device is coupled to the piston rod such that it slaves the piston rod when moved in the drive direction, but performs a movement counter to the drive direction without the piston rod. The piston rod and the driven device can be coupled via one or more transfer members. In one preferred embodiment, the piston rod and the driven device directly engage, causing the piston rod to be slaved. The engagement is releasable, in order to enable the reverse movement of the drive device, relative to the piston rod.

The piston rod can be mounted by the casing such that it can axially move back and forth. In this case, the product dosage to be delivered is set by adjusting an axially slight distance between a front end of the piston rod and the rear side of the piston by selecting the product. In this case, the piston rod forms the indicator of the drive device.

In some preferred embodiments, the piston rod is mounted by the casing such that it can be moved in the advancing direction but not counter to the advancing direction. In this case, movement counter to the advancing direction is at best possible in the course of exchanging the reservoir using corresponding assembly handles. In some preferred embodiments, however, restoring the piston rod is not possible. Rather, the administering apparatus is completely replaced by a new one. It would also be conceivable to divide the apparatus into a reservoir module designed as a disposable module and a dosing and drive module which can be repeatedly used with new reservoir modules. This design has already been successfully pursued in injection apparatus in the form of so-called semi-disposable injection pens and can also be advantageously used for the administering apparatus of the invention.

The fluid product to be administered or delivered may be a liquid for medical, therapeutic, diagnostic, pharmaceutical or cosmetic applications, or in combination for a number of these applications. The product can, for example, be insulin, a growth hormone, cortisone, collages or also liquid nutrients. In some embodiments, the administering apparatus is preferably used in applications in which a user administers the product himself/herself, as is usual in diabetes therapy. Application by trained staff only or also in the ward or outpatients field should not, however, be ruled out.

In the case of an injection apparatus, the product can be administered by suitable means, for example an injection cannula or a nozzle for needle-free injections. The injection can be subcutaneous, venous or intramuscular. In some embodiments, the administering apparatus can be an inhalation apparatus in which the product dosage selected or a remaining dosage still available in the reservoir is delivered from the reservoir, for example, into a chamber of the inhalation apparatus, and atomized by means of a vaporizer or other atomizing means, for inhalation. Furthermore, taking the product orally or administering the product via a feeding tube is also conceivable, to name but a few examples of administering.

DETAILED DESCRIPTION

Figure 1:
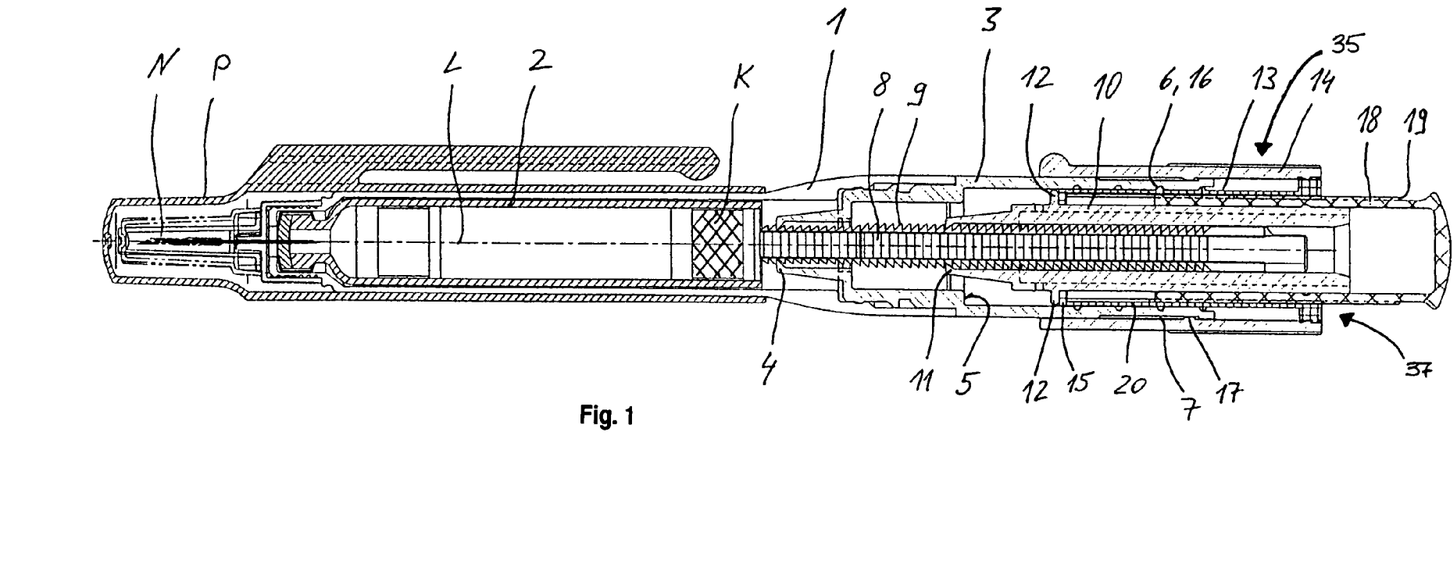
FIG. 1 depicts an injection apparatus in a longitudinal section.

FIG. 1 shows a complete longitudinal section of an injection apparatus. It is a gear rack pen for self-administering, for example, insulin or growth hormones. A first, front casing section 1 and a second, rear casing section 3 form a casing of the pen. The casing sections 1 and 3 are sleeve bodies. To form the casing, they are plugged into each other along a common central longitudinal axis L, in a non-releasable connection. Furthermore, the connection is such that the casing sections 1 and 3 cannot be moved relative to each other, either axially or rotationally about the longitudinal axis L.

An ampoule 2 accommodated in the front casing section 1 forms a reservoir for a product which is administered by way of injection using the pen. An outlet of the ampoule 2 is sealed by a membrane. An injection needle N is however guided through the membrane and protrudes via a rear end into the ampoule 2. A piston K is accommodated at a rear end of the ampoule 2 facing away from the outlet. An axial movement of the piston K along the longitudinal axis L in an advancing direction pointing towards the ampoule outlet delivers product from the ampoule 2 and through the injection needle N, thus administering it. In the state shown, the front casing section 1 is covered by an outer protective cap P and the injection needle N, still separate, is covered by an inner protective cap which of course has to be removed before administering.

The rear casing section 3 forms a mechanism holder by mounting a piston rod 8 acting on the piston K in the advancing direction and the other components of the pen, which participate in selecting a product dosage to be delivered and delivering the product dosage selected. These other components are a drive member 10 and an operating element 18 which together form a drive device 37 for the piston rod 8, and furthermore a dosing member 35 which in cooperation with the rear casing section 3 serves to select the product dosage to be delivered from the ampoule 2.

Figure 2:
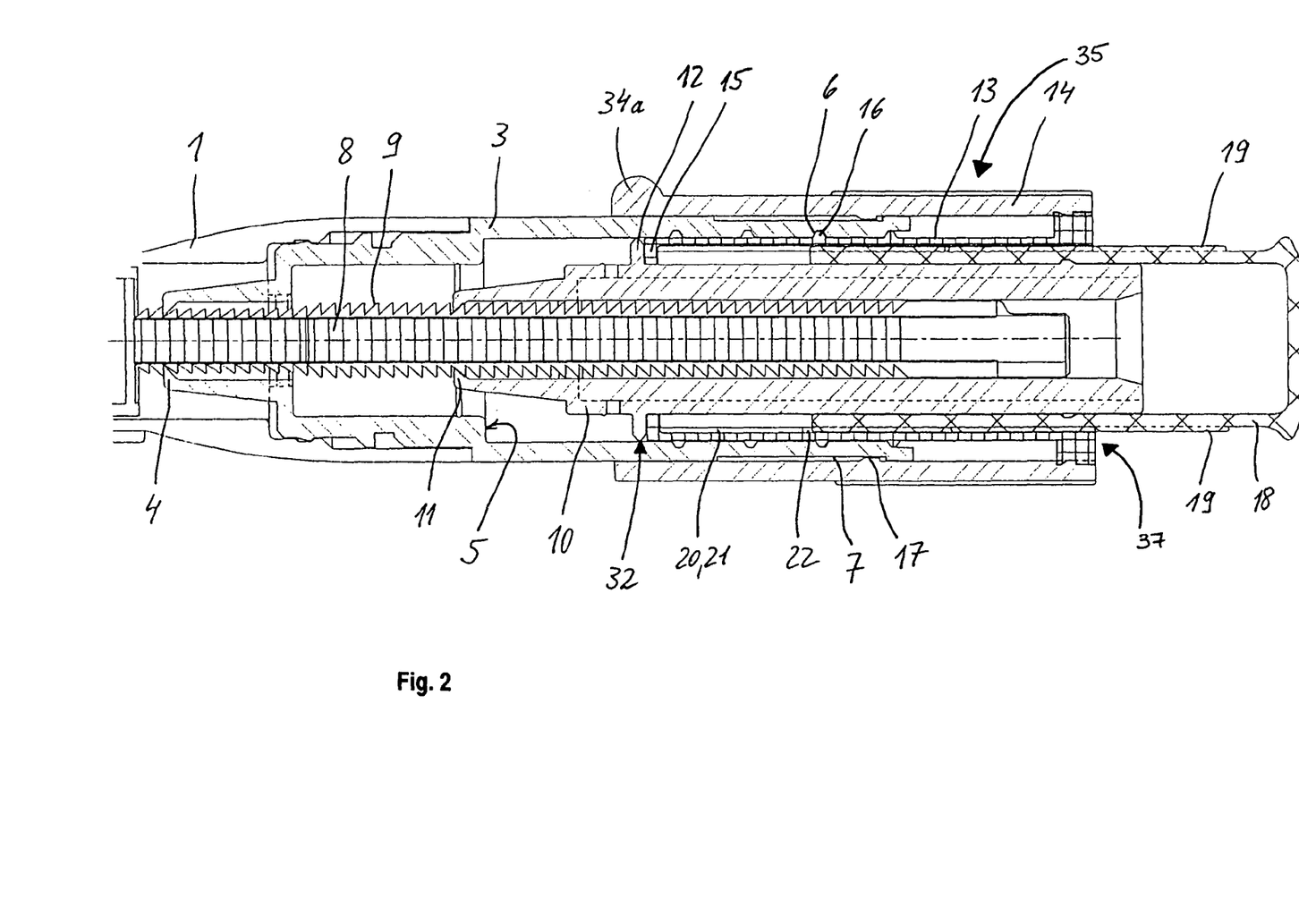
FIG. 2 depicts the rear part of the injection apparatus.

In FIG. 2, these components and their couplings are shown enlarged. Reference may also always be additionally made to the cross-sectional representation in FIG. 3. On the outer surface of the piston rod 8, four rows of teeth 9 formed from serrated teeth extend in the longitudinal direction, each offset by 90° with respect to each other. The rows of teeth 9 each exhibit the same separation. Each of the rows of teeth 9 is offset by a quarter pitch with respect to each of the other rows of teeth 9, in order to improve the dosing precision in a way known in its own right.

The rear casing section 3 forms blocking elements 4 which engage with the rows of teeth 9. The piston rod 8 is blocked by the engagement of the blocking elements 4, such that it is not possible to move the piston rod 8 counter to the advancing direction of the piston K. Movement of the piston rod 8 in the advancing direction, however, is permitted.

In order to advance the piston rod 8, the drive device 37 engages with the rows of teeth 9 of the piston rod 8 via slaving means 11, behind the blocking elements 4. The drive device 37 is formed by the sleeve-shaped drive member 10 and the sleeved-shaped operating element 18. The operating element 18 is pushed from behind onto the drive member 10. The connection between the drive member 10 and the operating element 18 is such that the operating element 18 cannot be axially moved relative to the drive member 10, but can be rotated about the longitudinal axis L relative to the drive member 10. The longitudinal axis L forms a translational axis of the drive device 37 and the driven device K, 8 consisting of the piston K and the piston rod 8, and furthermore, a rotational axis of the operating element 8.

The drive device 37 viewed as a whole protrudes through the dosing member 35. The slaving means 11 of the drive member 10 can be bent free, in particular free from the dosing member 35, elastically outwards from the mesh, in the radial direction, in order to enable the drive device 37 to move relative to the piston rod 8 counter to the advancing direction. The slaving means 11 are formed in a section of the drive device 37 protruding forwards out of the dosing member 35; in the example embodiment, they form the front end of the drive device 37. The engagement of the slaving means 11 and the shape of the rows of teeth 9 are such that the piston rod 8 is necessarily slaved by a movement of the drive device 37 in a drive direction directed towards the piston K, said drive direction being identical to the advancing direction.

In the depicts exemplary embodiment, the rows of teeth 9 are pointed in the advancing direction in a shape of serrated teeth. In modified embodiments, however, the piston rod 8 could comprise, instead of one or more rows of teeth 9, recesses or other engaging means for slaving means of a drive device, if it is only ensured that piston rod 8 is necessarily slaved in the advancing direction but is prevented from being slaved counter to the advancing direction.

The dosing member 35 is formed by a sleeve-shaped inner dosing body 13 and a sleeve-shaped outer dosing body 14, which are produced as separate parts and immovably connected to each other. In particular, it is not possible for the two dosing bodies 13 and 14 to either axially move or rotate about the longitudinal axis L relative to each other. The outer dosing body 14 concentrically surrounds the inner dosing body 13. A slight annular gap, into which the likewise sleeve-shaped rear casing section 3 protrudes, remains circumferential between the two dosing bodies 13 and 14.

The rear casing section 3, together with the dosing body 35, forms a swivel joint, more precisely a screw joint, which causes a rotational movement of the dosing member 35 about the longitudinal axis L to result in a translational movement of the dosing member 35 in or counter to the advancing direction, i.e., a axial translational movement relative to the rear casing section 3, depending on the direction of rotation. The longitudinal axis L forms a rotational axis and a translational axis of the dosing member 35. To form the swivel joint, the rear casing section 3 and the dosing member 35 are in threaded engagement. The threaded engagement is between an inner thread 6 formed on an inner surface area of the rear casing section 3 and an outer thread 16 formed on an outer surface area of the inner dosing body 13. Although less preferred, the threaded engagement could instead also be formed between an outer thread of the rear casing section 3 and an engaging inner thread of the outer dosing body 13. By rotating the dosing body 35, the user selects the product dosage to be administered. Since, through the threaded engagement, the dosing member 35 also simultaneously performs an axial translational movement, a delivery stroke of the length Ah is set for the drive device 37, which corresponds to the product dosage selected.

The inner dosing body 13 forms a dosing stopper 15 which limits the movement of the drive device 37 counter to the advancing direction. More precisely, a facing area of the dosing stopper 15 pointing in the advancing direction forms the dosing stopper 15 at its front end. The dosing stopper 15 is formed by an annular collar running around the longitudinal axis L, said collar protruding radially inwards towards the drive member 10 via an inner surface area of the inner dosing body 13. The dosing stopper 15, more precisely its front stopper area, runs around the longitudinal axis L at an axially constant height, i.e. a linear dosing stopper 15 is formed at a single height.

Opposite the dosing stopper 15 in the advancing direction, the rear casing section 3 forms a delivery stopper 5 which limits the movement of the drive device 37 in the advancing direction. The drive device 37 can thus be moved in and counter to the advancing direction between the delivery stopper 5, which is fixed to the casing and even formed by the rear casing section 3 itself, and the translationally adjustable dosing stopper 15. The drive device 37 in turn forms a counter stopper, namely the delivery and dosing stopper 12, on an outer surface area of the drive member 10. The delivery and dosing stopper 12 is formed by an annular collar via a front stopper area facing the delivery stopper 5 and a rear stopper area facing the dosing stopper 15. The delivery and dosing stopper 12 protrudes radially outwards from an outer surface area of the drive member 10 towards a facing inner surface area of the rear casing section 3.

The rear casing section 3 is completely transparent or at least transparent in the section which overlaps a maximum delivery stroke of the drive device 37. The transparency serves to verify the axial position of the drive device 37, in particular the position of the drive member 10 which engages directly with the piston rod 8 and is rigidly connected to it via the engagement in the advancing direction.

Figure 9:
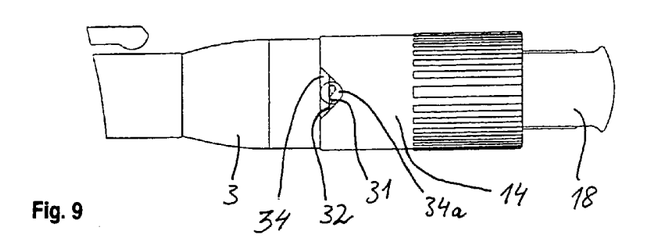
FIG. 9 depicts a view onto a dosage display in the apparatus state in FIG. 6.
Figure 10:
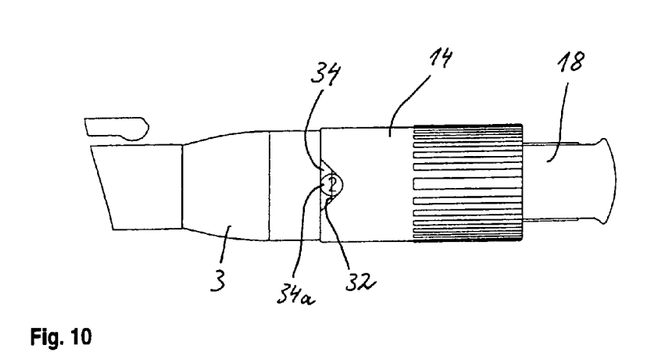
FIG. 10 depicts the view onto a dosage display after a "loading process" from the state in FIG. 9.
Figure 11:
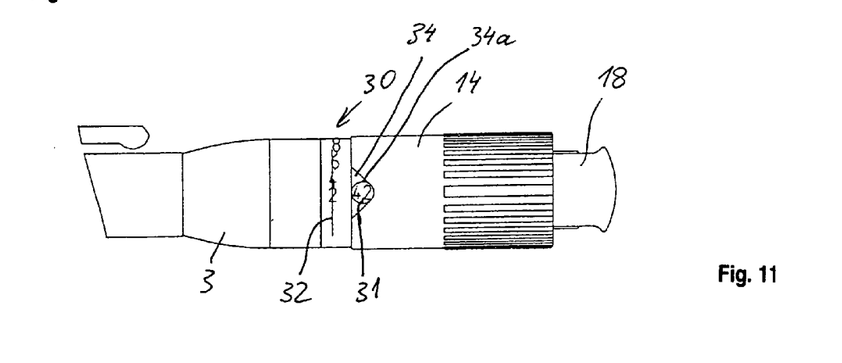
FIG. 11 depicts the view onto a dosage display in the apparatus state in FIG. 7.

For the purpose of a particularly precise optical verification, the drive member 10 is provided with a thin marking line, preferably a circumferential marking line, which is clearly visible through the rear casing section 3 and forms an indicator 32 (FIGS. 9 to 11). Advantageously, the delivery and dosing stopper 12 itself can form the marking line by forming a thin tip, radially outwards. The delivery and dosing stopper 12 is suitable as an indicator for verifying, alone because it radially protrudes almost directly up to the rear casing section 3 or even contacts it with sliding contact. The radially outer surface area of the delivery and dosing stopper 12 or the entire, radially outer tip is preferably additionally provided with a thin marking line which is attached on the surface or in a recess on the surface or is formed in the material, and can advantageously be fluorescent.

Figure 12:
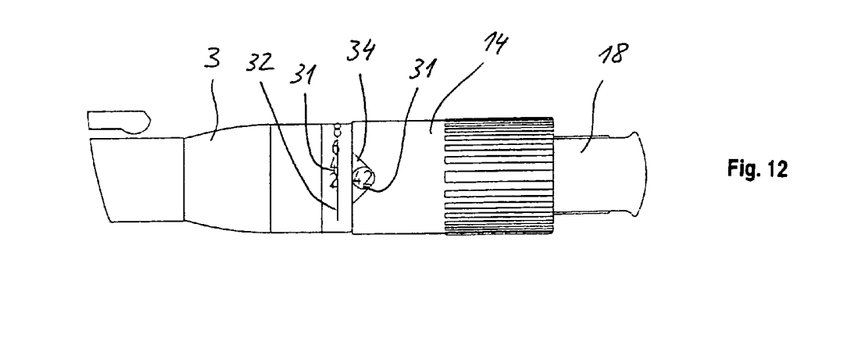
FIG. 12 depicts the view onto a dosage display in the apparatus state in FIG. 8.
Figure 13:
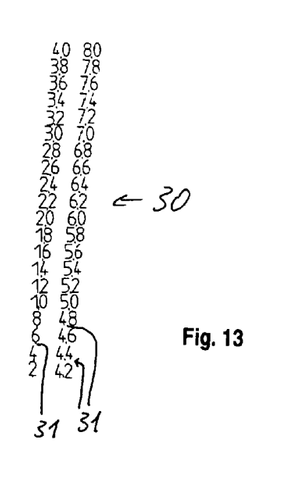
FIG. 13 depicts a dosage scale, unwound onto the plane of the page.

As may be seen in connection with FIGS. 9 to 12, and in particular in FIG. 13, the rear casing section 3 comprises a dosage scale 30 over the length of a maximum delivery stroke Ahmax. The dosage scale 30 can be attached to the inner surface area or more preferably to the outer surface area of the rear casing section 3 or let into the transparent surface of the rear casing section 3. In the example embodiment, it is attached to the outer surface area. The dosage scale 30 is formed by dosage numbers which indicate dosage units and by dosage marks 31. Each of the dosage numbers is each assigned to one of the dosage marks 31. The dosage marks 31 are formed by short, thin lines which each extend in the circumferential direction of the rear casing section 3. The dosage numbers are arranged over the circumference of the casing section 3, ascending towards the rear, in the form of spiral around the rotational axis L of the dosing member 35. Correspondingly, the dosage marks 31 are spirally arranged, such that each of the dosage marks 31 exhibits a different axial height to each of the other dosage marks 31. The dosage marks 31 thus represent, in a fine axial grading, every product dosage which can be selected and delivered in whole dosage units. Due to the transparency of the rear casing section 3, the axial position of the drive device 37 can be read, namely as the axial position which the indicator 32 of the drive device 37 assumes relative to the dosage marks 31. In the example embodiment, the cited marking line running around the longitudinal axis L on the radially outer tip of the delivery and dosing stopper 12 forms the indicator 32 of the drive device 37.

In order to make it easier to read the dosage scale 30, in particular for people with low visual acuity, the outer dosing body 14 comprises a viewing window 34 in a surface section which overlaps the dosage scale 30, said viewing window being developed into a magnifier 34a. The viewing window 34 is sufficiently large and of such a shape that precisely one of the dosage numbers of the dosage scale 30 can be identified as the dosage selected, through the viewing window 34. In the example embodiment, it is only ever possible to read exactly one dosage number through the viewing window.

In order that the dosage can be selected in discrete steps corresponding to the dosage numbers of the dosage scale 30, the dosing member 35 and the rear casing section 3 are each in releasable latching engagement in discrete rotational angular positions which the dosing member 35 can assume relative to the rear casing section 3. The latching engagement is formed between axially extending grooves 7 and engaging members 17 which engage with the grooves 7. In the example embodiment, the axial grooves 7 are let into the rear casing section 3 on the outer surface area. The engaging members 17 are correspondingly formed as short latching cams on the inner facing surface area of the outer dosing body 14. The engaging members 17 are linearly guided axially in the axial grooves 7 in each of the discrete rotational angular positions of the dosing member 35.

A rear end position of the dosing member 35 is defined by the engaging members 17 abutting a rear facing limiting area of the axial grooves 7. A front end position of the dosing member 35 is defined by a rear connecting stay, which the dosing bodies 13 and 14 form between themselves, abutting against a rear facing area of the rear casing section 3. The dosing member 35 can be adjusted back and forth, from rotational angular latching position to rotational angular latching position, between these two extreme dosing positions, in order to axially adjust the dosing stopper 15. The maximum delivery stroke Ahmax of the drive device 37 is as large as the axial distance which the dosing stopper 15 exhibits from the delivery stopper 5 in the rear end position of the dosing member 35 minus the axial thickness of the delivery and dosing stopper 12.

Although the user can at any time freely alter the product dosage set between the two extreme dosing positions, it is advantageous for most applications if a dosage, once set, no longer has to be altered. The injection apparatus can therefore be flexibly set to the needs of different users on the one hand, and used with an optimal setting for a particular user for repeatedly administering the same product dosage. In this sense, a dosage memory is also simultaneously obtained through the dosing member 35 which can be rotationally and translationally moved and therefore adjusted in combination, relative to the rear casing section 3.

One advantage which should by no means be neglected is that the dimensional accuracy and simply regulation of the dimensional accuracy and the stable design of the components which are decisive for dosing and delivery are realized using very few components. This contributes to the fact that the apparatus has a simply design and not least is therefore cheap, but nonetheless operates with precision and ensures exact dosing.

The nested arrangement of the dosing bodies 13 and 14 is also advantageous, providing multi-functionality of the dosing member 35 despite its simple construction. For the dosing member 35 directly forms the dosing engagement with the casing of the injection apparatus, the dosing stopper 15 for the drive device 37, a gripping part for the user and a part of a duplex dosage display, namely the display for the dosage selected on the one hand and the display for the dosage delivered on the other.

As a further advantage, the injection apparatus enables simple and reliable priming, i.e., bleeding the product-guiding parts between the piston K and the exit opening of the injection needle N.

Figure 3:
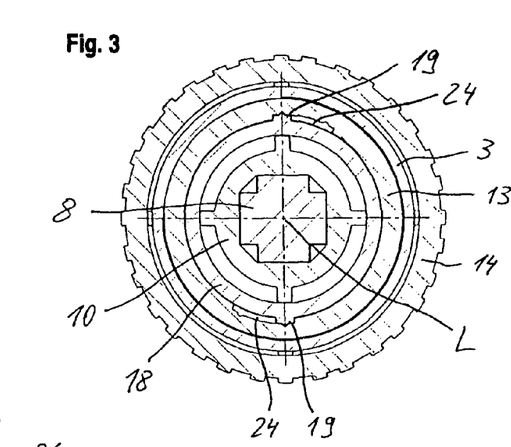
FIG. 3 depicts the injection apparatus in a cross-section.
Figure 4:
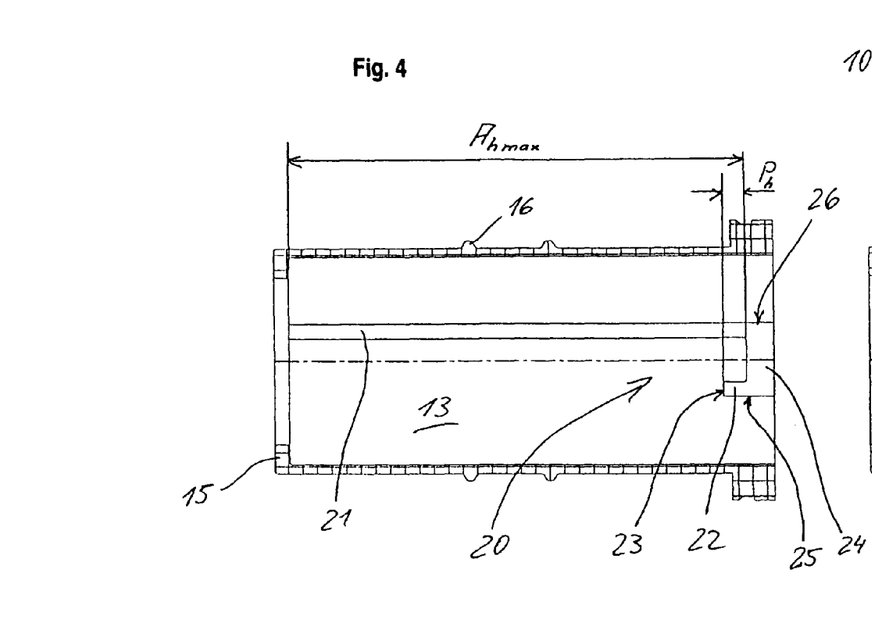
FIG. 4 depicts a dosing member of the injection apparatus in a longitudinal section.
Figure 5:
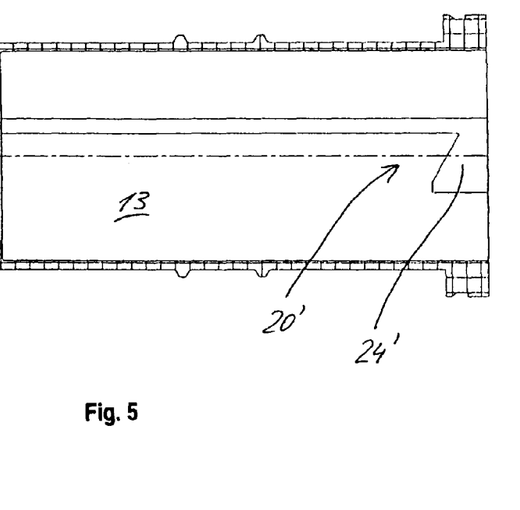
FIG. 5 depicts a modified dosing member in a longitudinal section.

To illustrate the priming function, reference is made to FIGS. 1 and 2 and in particular also to FIGS. 3, 4 and 5. In order to fulfill the priming function, the inner dosing body 13 and the operating element 18 are engaged. The engagement consists of a guiding curve and an engaging member which engages with the guiding curve. The engaging member can be moved in a defined manner in the guiding curve between axial stoppers on the one hand and radial stoppers on the other. The guiding curve on the one hand and the engaging member on the other are formed on the mutually facing surface areas of the inner dosing body 13 and the operating element 18.

As shown in FIGS. 3 and 4, the engaging member indicated as 19 is formed on an outer surface area of the operating element 18, while the guiding curve indicated as 20 is let into the facing inner surface area of the inner dosing body 13. The guiding curve 20 comprises a long axial section 21 and a contrastively short axial section 22 and a connecting section 24 which extends in the circumferential direction and connects the two axial sections 21 and 22 to each other, at their rear ends. The two side walls of the axial sections 21 and 22, which oppose each other in the circumferential direction in the area of the connecting section 24, form rotational stoppers 25 and 26 for the engaging member 19. The long axial section 21 extends in the advancing direction up to the dosing stopper 15, more precisely up to the rear facing area of the annular collar forming the dosing stopper 15. The shorter axial section 22 runs parallel to the axial section 21 and is formed as a short blind groove. A front facing area of the axial section 22 forms a priming stopper 23. The axial sections 21 and 22 feed onto the rear facing end of the inner dosing body 13. The connecting section 24 is correspondingly open at the rear facing end. The engaging member 19 is formed by an axial rib formed on the outer surface of the operating element 18. This axial rib forms the priming stopper on its free front facing area.

Because the engaging member 19 engages with the guiding curve 20 formed in this way, the operating element 18 can perform the shape of the movement corresponding to the guiding curve 20, relative to the inner dosing body 13, namely any selected delivery stroke Ah up to the maximum delivery stroke $Ah_{max}$, the contrastively smaller priming stroke Ph and the rotational selecting movement. Since the operating element 18 is connected to the drive member 10 such that it cannot move axially but can rotate about the longitudinal axis L, the operating element 18 can be rotated back and forth between the rotational stoppers 25 and 26 without acting on the drive member 10. Axial translational movement in either the long axial section 21 or the short axial section 22 is then only possible, however, together with the drive member 10.

Because the connecting section 24 is arranged on the rear ends of the axial sections 21 and 22, the rotational movement of the operating element 18 between the two rotational stoppers 25 and 26, i.e., from the delivery position to the priming position and vice versa, is only possible when the drive member 10 is abutting the dosing stopper 15 via its delivery and dosing stopper 12. In this "loaded" position, the engaging member 19 can be moved by rotating the operating element 18 relative to the inner dosing body 13 against the rotational stopper 25 and thus into axial flush with the priming stopper 23. In this rotational angular position of the operating element 18, the priming position, the drive device 37 can be moved in the advancing direction by axially pressing onto the operating element 18 up to the priming stopper 23. The axial length Ph of this priming stroke is only a few dosing units, for example two, three or four dosing units. The axial distance between the priming stopper 23 and the priming counter stopper which forms the engaging member 19 is correspondingly short.

It is advantageous if the operating element 18 is in releasable latching engagement with the inner dosing body 13 flush with the axial sections 21 and 22, i.e., on the rotational stoppers 25 and 26, respectively. In order to obtain the latching engagement with the inner dosing body 13 in each of the delivery position and the priming position, the engaging member 19 is again provided with a thin, axial latching cam on its narrow outer surface area, said latching cam coming to rest in the two rotational stopper positions of the operating element 18 in each of two axial latching grooves formed correspondingly in the guiding curve 20.

In the exemplary embodiment, two identical guiding curves 20 and engaging members 19 are provided which diametrically oppose each other.

In the variant of FIG. 4, the connecting section 24 runs, simply linearly, at a single axial height.

FIG. 5 shows a guiding curve 20 with a connecting section 24' whose front guiding wall leads from the priming stopper 23 obliquely backwards into the long axial section 21. Due to the oblique trajectory of the connecting section 24', a translational movement of the operating element 18—and together with it of the drive member 10—counter to the advancing direction and relative to the piston rod 8 is caused by a reverse rotational movement of the operating element 18 from the rotational stopper 25 towards the rotational stopper 26. In accordance with the embodiment of a priming process, the user therefore does not have to specially retract the drive device 37 again relative to the piston rod 8, i.e. load it. Rather, the winding or loading movement is forced by the reverse rotational movement. The guiding curve 20 in FIG. 5 otherwise corresponds to the guiding curve 20 in FIG. 4.

Figures 6, 7:
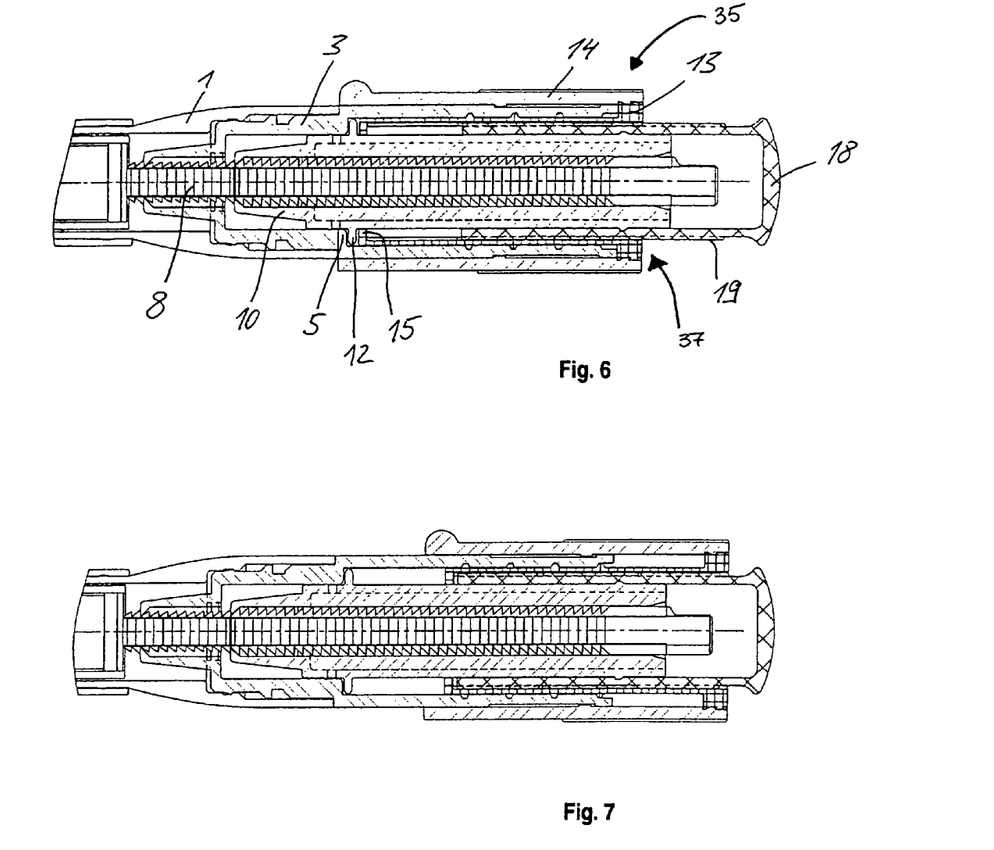
FIG. 6 depicts the rear part of the injection apparatus in a minimum-dosage state and "not loaded"
FIG. 7 depicts the rear part of the injection apparatus in a maximum-dosage state and "not loaded"

The functionality of an embodiment of an injection apparatus in accordance with the present invention will now be described. FIGS. 6 and 9 show the rear part of the injection apparatus in a longitudinal section, and each in a view in a state from which the dosage can be selected. Correspondingly, the drive device 37 abuts the delivery stopper 5, and the dosing member 35 assumes its axially front end position. A slight distance remains between the delivery and dosing stopper 12 of the drive device 37 and the dosing stopper 15 of the dosing member 35, said distance corresponding to two dosing units. Accordingly, the dosage of two dosage units can be read in the viewing window 34. Furthermore, the dosage mark 31 assigned to this dosage can also clearly be seen. Since the drive device 37 abuts the delivery stopper 5 via its delivery and dosing stopper 12, the marking line of the drive device 37 forming the indicator runs parallel to the dosage mark 31, with an axial distance. The distance corresponds to two dosage units. This situation can be seen in FIG. 9. The injection apparatus is "loaded" by retracting the drive device 37, relative to the piston rod 8, up to the dosing stopper 15. When this loading movement has been performed, two dosing units can be delivered by then advancing the drive device 37 and the thereby slaved piston rod 8. FIG. 10 shows this state, in which the drive device 37 abuts the dosing stopper 15 via its delivery and dosing stopper 12. The dosing mark 31 assigned to the dosage number "2" and the indicator overlap each other exactly.

From the state shown in FIGS. 6 and 9, the user selects the dosage. To select the dosage, the dosing member 35 has merely to be rotated about the longitudinal axis L relative to the rear casing section 3. Here, the outer dosing body 14 forms a gripping part and the inner dosing body 13 forms a dosing screw whose rotational movement is directly converted into the axial adjusting movement by the threaded engagement, for the purpose of selecting the dosage. The dosing is in discrete rotational angular positions which the dosing member 35 successively assumes relative to the rear casing section 3.

FIGS. 7 and 11 show the injection apparatus directly after the dosage has been selected. A dosage of 42 dosage units has been set, as can be read in the viewing window in FIG. 11. In the state shown in FIG. 7, selecting the dosage has been concluded but the injection apparatus is not yet "loaded", for the drive device 37 is still abutting the dosing stopper 5. This is indicated on the dosage scale 30 by the indicator 32, as can be seen in FIG. 11.

Figure 8:
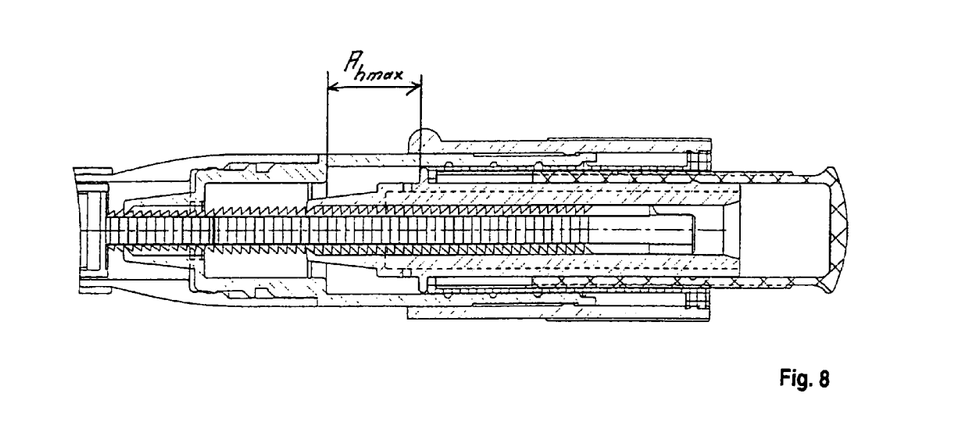
FIG. 8 depicts the rear part of the injection apparatus in a maximum-dosage state and "loaded"

FIG. 8 shows maximum dosing. FIG. 12 shows the injection apparatus in a state in which selecting the dosage has been concluded but the drive device 37 has not been retracted by the thus defined delivery stroke of length Ah, but rather only by a part of this stroke. In the state shown by way of example in FIG. 12, the drive device 37 has been retracted by a stroke corresponding to a product dosage of eight dosage units. This is indicated in FIG. 12 by the axial position of the indicator 32 on the dosage scale 30.

As illustrated in FIG. 12, a simple but reliable display of the remaining amount is obtained through the transparency of the rear casing section 3, the form of the indicator 32 and the arrangement of the dosage scale 30. If, namely, the ampoule no longer contains the full product dosage of, for example, 42 dosage units before the drive device 37 is retracted, then the drive device 37 can only be retracted counter to the advancing direction until the length of its next delivery stroke in the advancing direction corresponds to the product dosage still available in the ampoule 2 for a final delivery. In the exemplary embodiment, this remaining amount is eight dosage units. The indicator 32 and the dosage mark 31 assigned to the dosage of eight dosage units correspondingly overlap each other. The remaining amount which can be delivered is defined by a stopper acting between the piston rod 8 and the drive device 37. This stopper limits the effective length of the piston rod 8, i.e. the length by which the piston rod 8 can be moved as a whole in the advancing direction, from its position before a first delivery up until the ampoule 2 is evacuated. In the exemplary embodiment, the piston rod 8 forms this stopper for the slaving means 11 in its rear part, i.e., the slaving means 11 cannot elastically evade this stopper.

In the foregoing description, embodiments of the invention, including preferred embodiments, have been presented for the purpose of illustration and description. They are not intended to be exhaustive or to limit the invention to the precise form disclosed. Obvious modifications or variations are possible in light of the above teachings. The embodiments were chosen and described to provide the best illustration of the principals of the invention and its practical application, and to enable one of ordinary skill in the art to utilize the invention in various embodiments and with various modifications as are suited to the particular use contemplated. All such modifications and variations are within the scope of the invention as determined by the appended claims when interpreted in accordance with the breadth they are fairly, legally, and equitably entitled.

The invention claimed is:

1. An administering apparatus with a dosage display, comprising:
   a) a casing comprising a front casing section and a rear casing section, and a reservoir for a fluid product, wherein the front casing section and the rear casing section are plugged into each other along a common central longitudinal axis, in a non-releasable connection, whereby the front casing section and the rear casing section cannot be moved relative to each other, either axially or rotationally about the longitudinal axis;
   b) a driven device which acts on said product contained in said reservoir, in order to deliver product;
   c) a dosing means, using which a product dosage to be delivered can be selected, and which comprises a dosage scale with a number of dosage marks axially spaced out from each other; and
   d) a drive device coupled to said driven device for driving the driven device, said drive device performing a delivery stroke from an initial position, in a drive direction, up to a delivery stopper, the length of said delivery stroke counter to the drive direction being limited by selecting the product dosage by said dosing means;
   e) wherein said casing is transparent, at least in an area overlapping said dosage scale;
   f) the drive device carries an indicator marking, in order to indicate the initial position of the drive device through the transparent area of the casing, relative to said dosage marks;
   g) the driven device comprises a piston and a piston rod acting on the piston in the drive direction to deliver product from the reservoir by axially moving the piston in the drive direction, wherein the drive device is moveable counter to the drive direction as far as an adjustable dosing stopper, and the piston rod is prevented from moving counter to the drive direction and is coupled to the drive device such that it is slaved by the drive device in the drive direction; and wherein
   h) an outer surface of the piston rod comprises rows of teeth, the rear casing section comprising blocking elements which engage the rows of teeth such that the piston rod is permitted to move in an advancing direction but not counter to the advancing direction.

2. The administering apparatus as set forth in claim 1, wherein the dosing means comprises another indicator, in order to display the product dosage selected on the dosage scale or on another dosage scale.

3. The administering apparatus as set forth in claim 1, wherein the dosing means comprises a dosing member which performs a dosing movement relative to the casing, in order to select the product dosage to be delivered, and wherein the position of said dosing member is displayed on the dosage scale or on another dosage scale.

4. The administering apparatus as set forth in claim 3, wherein the dosing member is coupled to the casing such that it can be rotated about a rotational axis pointing in the drive direction.

5. The administering apparatus as set forth in claim 1, wherein the dosage marks are also spaced out from each other in the circumferential direction, around an axis pointing in the drive direction.

6. The administering apparatus as set forth in claim 1, wherein the casing is a support for the dosage scale for displaying the initial position of the drive device.

7. The administering apparatus as set forth in claim 1, wherein the dosing means comprises a dosing member which performs a dosing movement relative to the casing, in order to select the product dosage to be delivered, and forms another indicator which displays the product dosage selected on the dosage scale or another dosage scale.

8. The administering apparatus as set forth in claim 1, wherein the dosage scale serving to display the initial position of the drive device comprises a clearly assigned dosage symbol for at least a part of the dosage marks, said dosage symbol representing a product dosage corresponding to the assigned dosage mark.

9. The administering apparatus as set forth in claim 1, wherein the drive device comprises a marking line on an outer surface area facing the casing, said marking line extending perpendicular to the drive direction and forming the indicator marking of the drive device.

10. The administering apparatus as set forth in claim 1, wherein the dosage marks are formed by lines which extend perpendicular to the drive direction.

11. The administering apparatus as set forth in claim 1, wherein said administering apparatus is an injection apparatus comprising an injection cannula of at most 30 gauge, or an injection cannula having an outer diameter of at most 320 μm and an inner diameter not specified in ISO 9626, wherein the wall thickness is thinner than is specified in ISO 9626.

12. The administering apparatus as set forth in claim 11, wherein said injection cannula is 31 or 32 gauge.

13. The administering apparatus as set forth in claim 1, wherein the drive device performs a delivery stroke in a drive direction and can only be moved relative to the driven device opposite the drive direction, by a path length which corresponds to a remaining dosage in the reservoir.

14. The administering apparatus as set forth in claim 1, wherein said rear casing section is transparent.

15. The administering apparatus as set forth in claim 1, wherein said reservoir for said product is a disposable module, and at least one of said front or rear casing sections is disposable.

16. An administering apparatus with a dosage display, comprising:
   a) a casing comprising a front casing section and a rear casing section, and a reservoir for a fluid product, wherein the front casing section and the rear casing section are plugged into each other along a common central longitudinal axis, in a non-releasable connection, whereby the front casing section and the rear casing section cannot be moved relative to each other, either axially along or rotationally about the longitudinal axis;
   b) a driven device which acts on said product contained in said reservoir, in order to deliver product;
   c) a dosing means, using which a product dosage to be delivered can be selected, and which comprises a dosage scale with a number of dosage marks axially spaced out from each other; and
   d) a drive device coupled to said driven device for driving the driven device, said drive device performing a delivery stroke from an initial position, in a drive direction, up to a delivery stopper, the length of said delivery stroke counter to the drive direction being limited by selecting the product dosage by means of said dosing means;
   e) wherein said casing is transparent, at least in an area overlapping said dosage scale;
   f) wherein the drive device carries an indicator marking, in order to indicate the initial position of the drive device through the transparent area of the casing, relative to said dosage marks;
   g) wherein the dosing means comprises another indicator, in order to display the product dosage selected on the dosage scale or on another dosage scale;
   h) said indicator marking of the drive device and said other indicator overlap in the initial position of the drive device, if the drive device can perform the maximum stroke, set by selecting the product dosage, from the initial position;
   i) the driven device comprises a piston and a piston rod acting on the piston in the drive direction to deliver product from the reservoir by axially moving the piston in the drive direction, the drive device moveable counter to the drive direction to an adjustable dosing stopper, and the piston rod is prevented from moving counter to the drive direction and is coupled to the drive device such that it is slaved by the drive device in the drive direction; and wherein
   j) an outer surface of the piston rod comprises rows of teeth, the rear casing section comprising blocking elements which engage the rows of teeth whereby the piston rod is permitted to move in an advancing direction but not against the advancing direction.

17. The administering apparatus as set forth in claim 16, wherein said reservoir for said product is a disposable module, and a portion of said casing is disposable.

18. An administering apparatus with a dosage display, comprising:
   a) a casing comprising a front casing section and a rear casing section, and a reservoir for a fluid product, wherein the front casing section and the rear casing section are non-releaseably connected to each other along a common central longitudinal axis, and cannot be moved relative to each other, either axially along or rotationally about the longitudinal axis;
   b) a driven device which acts on said product contained in said reservoir, in order to deliver product;
   c) a dosing means, using which a product dosage to be delivered can be selected, and which comprises a dosage scale with a number of dosage marks axially spaced out from each other; and
   d) a drive device coupled to said driven device for driving the driven device, said drive device performing a delivery stroke from an initial position, in a drive direction, up to a delivery stopper, the length of said delivery stroke counter to the drive direction being limited by selecting the product dosage by means of said dosing means;
   e) wherein said casing is transparent, at least in an area overlapping said dosage scale;
   f) wherein the drive device carries an indicator marking, in order to indicate the initial position of the drive device through the transparent area of the casing, relative to said dosage marks;
   g) wherein the dosing means comprises a dosing member which performs a dosing movement relative to the casing, in order to select the product dosage to be delivered, and wherein the position of said dosing member is displayed on the dosage scale or on another dosage scale;
   h) the dosing member and the casing are coupled via a swivel joint, such that a rotational movement of the dosing member about a rotational axis pointing in the drive direction causes an axial translational movement of the dosing member;
   i) the driven device comprises a piston and a piston rod acting on the piston in the drive direction to deliver product from the reservoir by axially moving the piston in the drive direction, the drive device moveable counter to the drive direction to an adjustable dosing stopper, and the piston rod is prevented from moving counter to the drive direction and is coupled to the drive device such that it is slaved by the drive device in the drive direction; and wherein
   j) an outer surface of the piston rod comprises rows of teeth, the rear casing section comprising blocking elements which engage the rows of teeth such that the piston rod is permitted to move in an advancing direction but not counter to the advancing direction.

19. An administering apparatus with a dosage display, comprising:
   a) a casing comprising a front casing section and a rear casing section, and a reservoir for a fluid product, wherein the front casing section and the rear casing section are plugged into each other along a common central longitudinal axis in a non-releasable connection, whereby the front casing section and the rear casing section cannot be moved relative to each other, either axially along or rotationally about the longitudinal axis;

b) a driven device which acts on said product contained in said reservoir, in order to deliver product;

c) a dosing means, using which a product dosage to be delivered can be selected, and which comprises a dosage scale with a number of dosage marks axially spaced out from each other; and d) a drive device coupled to said driven device for driving the driven device, said drive device performing a delivery stroke from an initial position, in a drive direction, up to a delivery stopper, the length of said delivery stroke counter to the drive direction being limited by selecting the product dosage by means of said dosing means;

e) wherein said casing is transparent, at least in an area overlapping said dosage scale;

f) wherein the drive device carries an indicator marking, in order to indicate the initial position of the drive device through the transparent area of the casing, relative to said dosage marks;

g) the dosing means comprises a dosing member comprising an inner dosing body and an outer dosing body, between which a gap is formed into which the casing protrudes, wherein said inner dosing body forms a dosing stopper for selecting the product dosage, wherein said dosing stopper can be adjusted in or counter to the drive direction by operating said outer dosing body;

h) the driven device comprises a piston and a piston rod acting on the piston in the drive direction to deliver product from the reservoir by axially moving the piston in the drive direction, the drive device moveable counter to the drive direction up to an adjustable dosing stopper, and the piston rod prevented from moving counter to the drive direction and slaved to the drive device in the drive direction; and wherein i) an outer surface of the piston rod comprises rows of teeth and the rear casing section comprises blocking elements which engage the rows of teeth whereby the piston rod is moveable in an advancing direction but not counter to the advancing direction.

20. The administering apparatus as set forth in claim 19, wherein the dosage marks are also spaced out from each other in the circumferential direction, around an axis pointing in the drive direction.

21. The administering apparatus as set forth in claim 19, wherein the dosage scale serving to display the initial position of the drive device comprises a clearly assigned dosage symbol for at least a part of the dosage marks, said dosage symbol representing a product dosage corresponding to the assigned dosage mark.

22. The administering apparatus as set forth in claim 19, wherein the drive device comprises a marking line on an outer surface area facing the casing, said marking line extending perpendicular to the drive direction and forming the indicator marking of the drive device.

23. The administering apparatus as set forth in claim 19, wherein the dosage marks are formed by lines which extend perpendicular to the drive direction.

24. An administering apparatus with a dosage display, comprising:

a) a casing comprising a front casing section and a rear casing section, and a reservoir for a fluid product, wherein the front casing section and the rear casing section are non-releaseably connected along a common central longitudinal axis and cannot be moved relative to each other axially along or rotationally about the longitudinal axis;

b) a driven device which acts on said product contained in said reservoir, in order to deliver product;

c) a dosing means, using which a product dosage to be delivered can be selected, and which comprises a dosage scale with a number of dosage marks axially spaced out from each other; and d) a drive device coupled to said driven device for driving the driven device, said drive device performing a delivery stroke from an initial position, in a drive direction, up to a delivery stopper, the length of said delivery stroke counter to the drive direction being limited by selecting the product dosage by means of said dosing means;

e) wherein said casing is transparent, at least in an area overlapping said dosage scale;

f) wherein the drive device carries an indicator marking, in order to indicate the initial position of the drive device through the transparent area of the casing, relative to said dosage marks;

g) the dosing means comprises a dosing member which forms a dosing stopper, can be moved counter to the drive direction up to the drive device, and is movably coupled to the casing, in order to select the product dosage by adjusting said dosing stopper relative to the casing;

h) the driven device comprises a piston and a piston rod acting on the piston in the drive direction to deliver product from the reservoir by axially moving the piston in the drive direction, the drive device moveable counter to the drive direction to an adjustable dosing stopper, and the piston rod is prevented from moving counter to the drive direction and is coupled to the drive device such that it is slaved by the drive device in the drive direction; and wherein i) an outer surface of the piston rod comprises rows of teeth, and the rear casing section comprises blocking elements which engage the rows of teeth such that the piston rod is permitted to move in an advancing direction but not counter to the advancing direction.

25. The administering apparatus as set forth in claim 24, wherein said administering apparatus is an injection apparatus comprising an injection cannula of at most 30 gauge, or an injection cannula having an outer diameter of at most 320 µm and an inner diameter not specified in ISO 9626, wherein the wall thickness is thinner than is specified in ISO 9626.

26. The administering apparatus as set forth in claim 25, wherein said injection cannula is 31 or 32 gauge.

27. The administering apparatus as set forth in claim 24, wherein the casing is a support for the dosage scale for displaying the initial position of the drive device.

* * * * *